United States Patent
Gertzman et al.

[11] Patent Number: 6,162,225
[45] Date of Patent: Dec. 19, 2000

[54] ALLOGRAFT BONE FIXATION SCREW METHOD AND APPARATUS

[75] Inventors: Arthur A. Gertzman, Stony Point, N.Y.; Timothy G. Haines, Minneapolis, Minn.

[73] Assignee: Musculoskeletal Transplant Foundation, Edison, N.J.

[21] Appl. No.: 09/178,684

[22] Filed: Oct. 26, 1998

[51] Int. Cl.[7] .................................................. A61B 17/56
[52] U.S. Cl. ............................................................. 606/73
[58] Field of Search ...................... 606/232, 73; 411/310, 411/500–510, 399, 401, 409, 400

[56] References Cited

U.S. PATENT DOCUMENTS

| | | |
|---|---|---|
| 172,351 | 1/1876 | Sloan . |
| 173,356 | 2/1876 | Sloan . |
| 755,804 | 3/1904 | Smith . |
| 1,300,275 | 4/1919 | Johnson . |
| 1,336,794 | 4/1920 | Stepanian . |
| 4,128,038 | 12/1978 | Urwin ........................... 85/45 |
| 4,463,753 | 8/1984 | Gustilo ...................... 128/92 B |
| 4,724,731 | 2/1988 | Onofrio ......................... 81/119 |
| 4,823,650 | 4/1989 | Tuttle ......................... 81/124.2 |
| 5,012,624 | 5/1991 | Dahlgren .................... 81/124.2 |
| 5,367,926 | 11/1994 | Mikic et al. .................. 81/436 |
| 5,403,136 | 4/1995 | Mathys ......................... 411/310 |
| 5,433,569 | 7/1995 | Fall et al. ..................... 411/387 |
| 5,443,482 | 8/1995 | Stone et al. .................. 606/232 |
| 5,730,744 | 3/1998 | Justin et al. ................... 606/73 |
| 5,968,047 | 10/1999 | Reed . |

OTHER PUBLICATIONS

F. Albee, *Bone Graft Surgery in Disease, Injury and Deformity*, p. 22 (1940).
F. Albee, *The Improved Albee Bone Mill*, American Journal of Surgery, p. 657 (Mar., 1938).

*Primary Examiner*—Michael H. Thaler
*Assistant Examiner*—Tan-Uyen T. Ho
*Attorney, Agent, or Firm*—John S. Hale; Gipple & Hale

[57] ABSTRACT

A combination driver and bone screw assembly comprising a screw shank with a uniform diameter threaded portion, an unthreaded portion with a outwardly tapered end and a driving end portion of substantially wedge shaped configuration which can be engagably seated in a wedge shaped notch seat of a driver member. The driver member comprises a body, a drive head defining a wedge shaped notch seat secured to the body forming a shoulder and a drive collar mounted around the drive head and seated on the shoulder.

In operation a bore is drilled in the patients bone with the top portion of the bore having a tapered geometry which widens from the diameter of the bore. The bone screw driving end portion is placed in the wedge shaped notch seat of a driver member and a drive collar is mounted around the driver drive head and engages the shoulder. The driver member is rotated driving the bone screw into the previously cut bore in the patients bone until the tapered surface of the bore engages the tapered undercut surface of the screw.

38 Claims, 4 Drawing Sheets

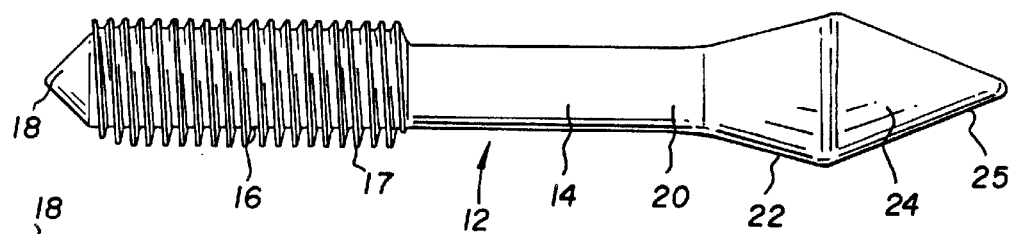
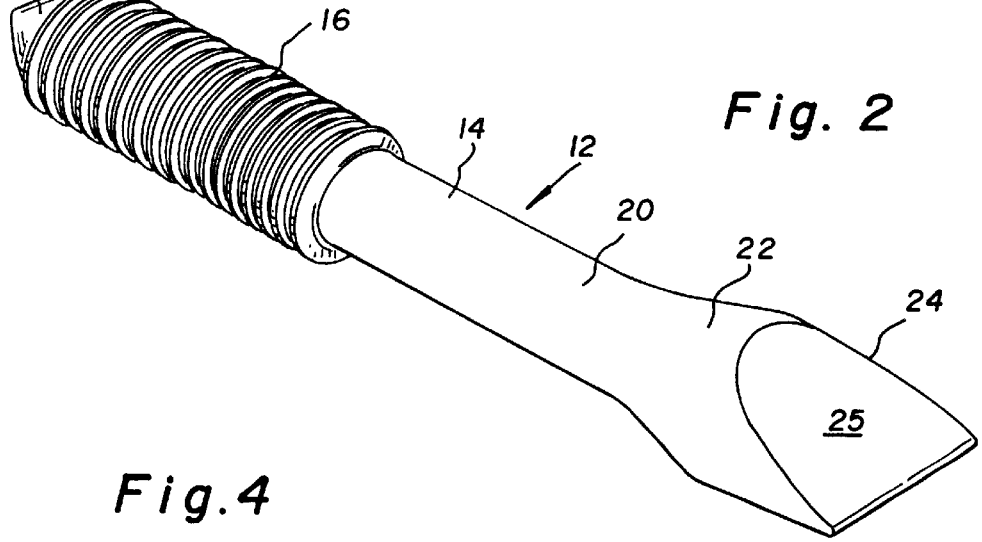
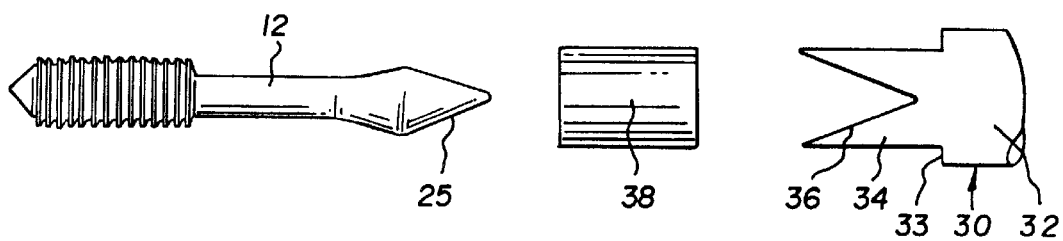
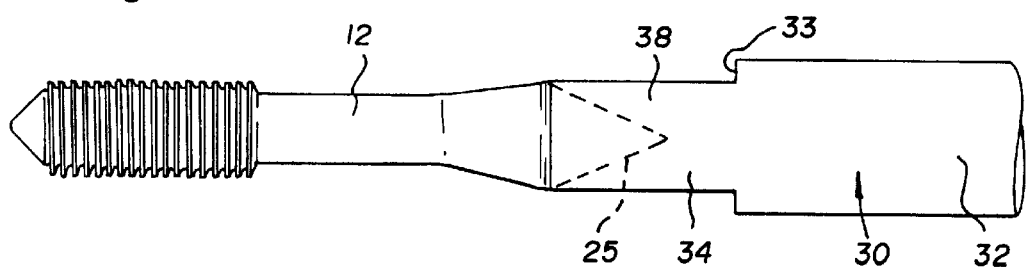

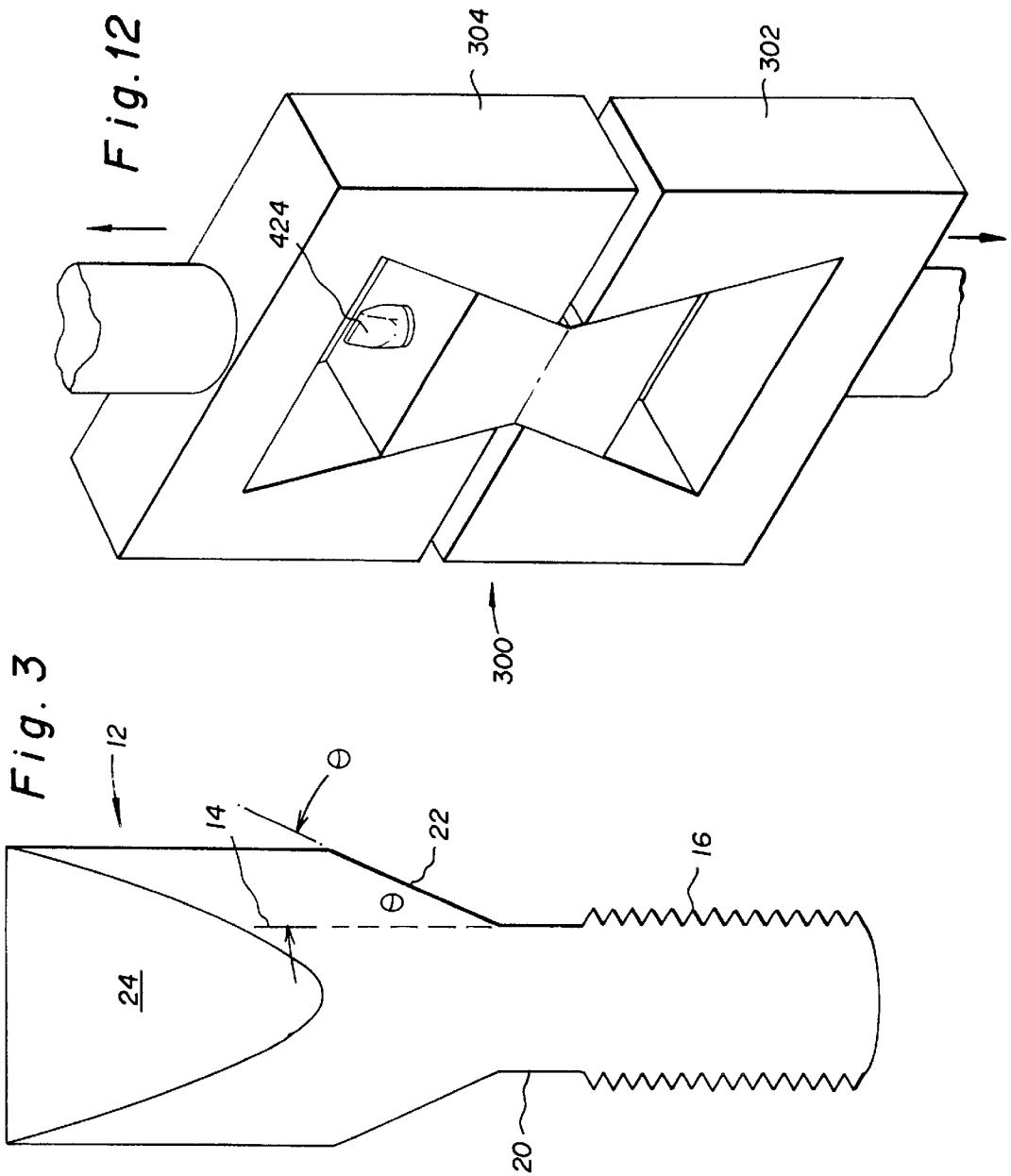

FRACTURE SITE

ALLOGRAFT BONE FIXATION SCREW
METHOD AND APPARATUS

BACKGROUND OF THE INVENTION

1. Field of Invention

The present invention relates to threaded devices used to facilitate bone fracture or osteotomy fixation in human surgery.

2. Description of the Prior Art

The prior art contains many references directed to fastener drivers which drive screws having a Phillips head, standard slot head or other heads having various shaped slots or recesses which receive the torque from the driver end. See for example the prior art shown in U.S. Pat. No. 5,367,926. There are other examples of prior art fastener drivers having female driver ends which receive and drive fasteners having a male torque receiving end. Typical driver screw fasteners and screws of such a construction are shown in U.S. Pat. Nos. 755,804; 1,300,275; 4,724,731; 5,012,624; 5,443,482 and 5,730,744. Wrenches having a female driving end which drive caps or nuts are shown by U.S. Pat. Nos. 1,336,794 and 4,823,650.

Several patents such as U.S. Pat. Nos. 172,351 and 173,356 show screws having a head formed with a wedge shaped groove or slot which receives the angular notch of a driver head to transmit torque and drive the screw. While most screws have a uniform diameter shank, U.S. Pat. Nos. 4,463,753 and 5,403,136 disclose bone screws which have a tapered shank which cause compression of the bone between the distal end of the screw and the taper.

Millions of people suffer from a variety of musculoskeletal disorders or traumatic occurrences necessitating the use of devices to reduce osteotomies or fractures. Many different means have been developed to facilitate fixation and healing of the traumatized bone tissue. In the past, metallic pins and screws have been used to establish initial mechanical stability of the trauma site, and to facilitate permanent, mechanically stabile fracture or osteotomy healing.

The most significant difficulties with screws and pins currently used to facilitate fixation include the residual presence of "hardware" that may migrate, include adverse tissue reaction to the presence of foreign particulate debris, and otherwise compromise the functionality of the fixation. Some recently offered products feature bioresorbable material technology which allows for gradual absorption of the screws and pins. Unfortunately, these materials may fall short of expected performance due to incomplete osseointegration of patient bone. Allograft bone offers a suitably strong, biocompatible, and bioresorbable material that addresses these deficiencies.

Screws made completely of allograft bone have been described in F. Albee, *Bone Graft Surgery in Disease, Injury and Deformity* p. 22 (1940); and F. Albee, *The Improved Albee Bone Mill*, American Journal of Surgery p. 657 (March 1938). These screws offer the advantage of the biointegration of allograft bone tissue. However, the conventional slotted or rectangular head designs commonly used in metal screws when used with allograft bone screws, result in premature failure of the screws during intraoperative insertion due to excessively high shear forces applied to the head (see FIG. 10) and the transition between the head and threaded portion of the screw. This shearing is due to several factors. First, and foremost, while bone is quite strong in compressive loading, it is relatively weak in tension and shear. Since the torque applied to a screw induces shear stresses, the design of a screw made of allograft bone tissue must be as robust as necessary with respect to torque loading.

SUMMARY OF THE INVENTION

In response to the needs still left unresolved by the prior art devices, the present invention contemplates an allograft bone screw made of cortical bone with a unique head design which solves the deficiencies of the prior art prostheses.

The inventive screw design offers two unique features which fulfill the potential of allograft bone as an ideal material for screws used in fracture and osteotomy reduction. The first unique feature is the wedge shaped drive head which mates with a specialized driver used to apply torque to the screw. This wedge shape accomplishes two desirable functions. The first function is that it avoids localized tensile stresses inherent in standard drive designs that would lead to mechanical failure of an allograft bone screw and the second function is the ability of this screw head geometry to act as a torque limiting means that also avoids mechanical failure of the screw. The second unique feature is an outwardly tapering shank portion adjacent the wedge shaped head which provides an undercut for the head providing a tight engagement of the screw in the bone bore.

Thus the present screw design is both easy to use and offers the ideal physiological response of patient tissue to allograft bone tissue.

In another aspect of the invention, a method is provided for implanting the bone screw in the bone body. The approach includes the steps of drilling a bore in the bone with a drill having a tapered proximal end so that a portion of the bore opens into a cone having a wider diameter then the diameter of the bore. The bone screw head is then mounted in a V shaped notch cut in the driver head and a sleeve is mounted on the driver around the bone screw head and is seated on a shoulder formed by the difference in diameter of the driver head and the driver body to keep the screw head seated in the notch. The bone screw is then driven or screwed into the prepared bone bore.

These and other objects, advantages, and novel features of the present invention will become apparent when considered with the teachings contained in the detailed disclosure along with the accompanying drawings.

BRIEF DESCRIPTION OF THE DRAWINGS

FIG. 1 is a side elevational view of the inventive bone fixation screw;

FIG. 2 is a perspective view of the inventive bone fixation screw shown in FIG. 1;

FIG. 3 is a schematic view of the inventive bone fixation screw shown in FIGS. 1 and 2;

FIG. 4 is an exploded view of the bone fixation screw and driver assembly;

FIG. 5 is a side elevational view partially in phantom of the bone fixation screw mounted in the drive head of the drive assembly;

FIG. 12 is a front elevational view of the testing block used in testing the inventive bone fixation screw.

DETAILED DESCRIPTION OF PREFERRED EMBODIMENT

The preferred embodiment and the best mode of the present invention is shown in FIGS. 1 through 5.

Figure 8:
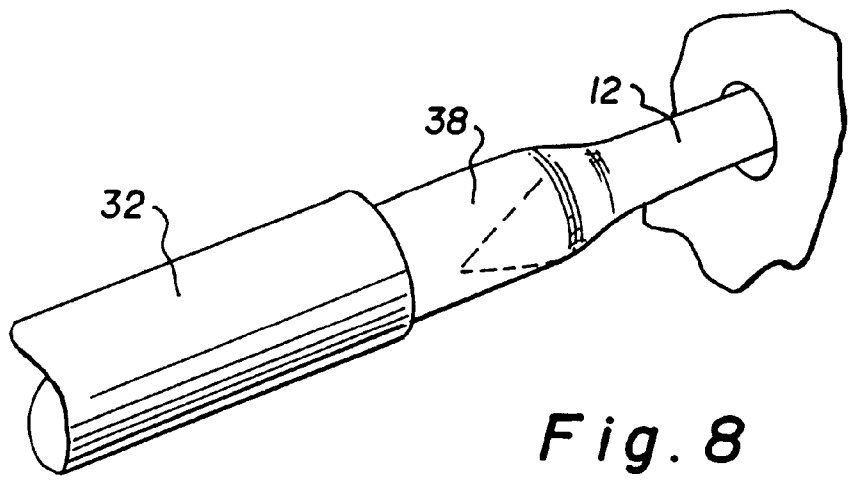
FIG. 8 is a perspective view of another embodiment of the screw showing a taper lock.
Figure 11:
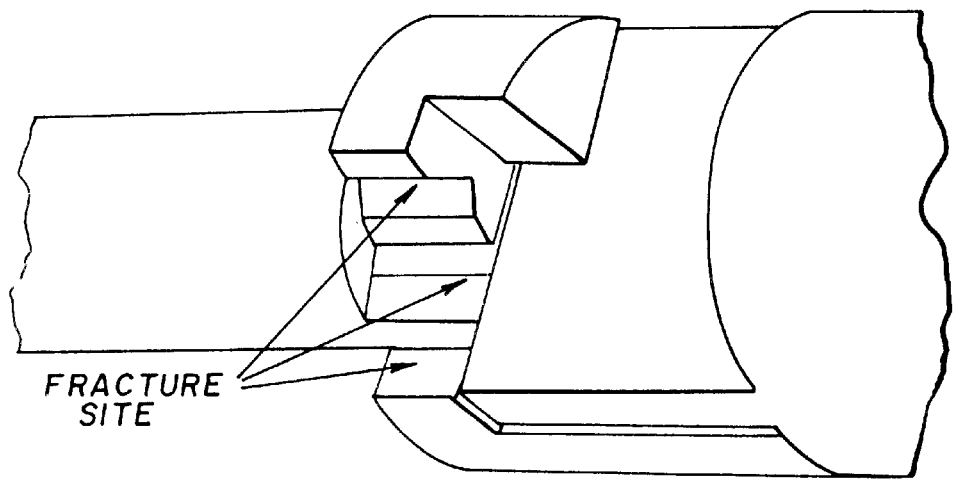
FIG. 11 is a broken away view of FIG. 10 showing the fracture site of prior art Phillips screw heads.

It is an accepted fact that the initiation of mechanical failure in a material occurs at the outer surface of the material. Also, it is recognized that rapid changes in cross sectional geometry act as localized "stress risers", significantly increasing the risk of failure under load. The present inventive bone screw 12 solves these problems particularly when the screw is constructed of allograft bone, deformable plastic or fracturable material. The preferred material is either cortical or cancellous allograft bone. The bone fixation screw 12 has a shank 14 with a threaded portion 16 ending in a distal pointed tip 18 and an unthreaded portion 20 which is tapered outward at 22 ending in a wedge shaped head 24. The tapered portion 22 of the shank 14 is preferably tapered at an angle ranging from 10° to 45° from the center axis of the shank. As shown in FIG. 3 the tapered portion 22 forms an angle theta (Θ) with a line drawn along the longitudinal axis of the shank 14. This angle Θ is about equal to or less than 20° for use in cortical bone and about equal to or greater than 20° for use in cancellous bone. The overall length of the screw is preferably about 1 to 1¼ inches and the shank has a 3.5 mm diameter. The bevel of the thread is preferably about 60°. However the included angle at the thread root an vary from 10° to 80°. It will be appreciated that these dimensions are preferred dimensions and may be varied while retaining the structure and function of the invention without limiting same. The threaded portion 16 preferably is formed with a single helical thread 17 formed on the exterior surface of the shank to engage the bone material 100 and draw the screw 12 down into the bore 102. The thread 17 can be a #6-32 UNC, a #6-40 UNS or BA4 (British Aircraft) thread. UNC and UNS threads have a helical generally V-shaped thread with a 60° bevel. Other screw threads which can be used are standard screw threads (ANSI): #0, #1, #2, #3, #4, #5, #6, #8, #10, #12 and ¼ inch, 5/16 inch and 3/8 inch. Metric threads M 1.6, M 2, M 2.5, M 3, M 4, M 5, M 6, M 8 and M 10 can also be used. It is also contemplated that the threaded portion 16 may include a self-tapping thread having grooves extruded along the longitudinal axis of the threads providing sharp leading edges and space for removal of osseous debris. One example of a self-tapping thread is where the leading edge of the thread is sharp with the following edge being generally of a rectangular profile. The self-tapping aspect of the threaded portion facilitates insertion and anchoring of the screw into a patient's bone. The drive head 24 geometry embodies gradual changes in cross-sectional geometry and avoids excessive localized tensile loading on the surface of the drive geometry. If standard slot or "Phillips" style device geometry were used (FIG. 8), the rapid change in cross section and localized contact stresses between the screw and screwdriver would lead to catastrophic failure of the screw during intraoperative insertion and application of torque (FIG. 11).

This drive geometry also acts as a torque limiter due to the ability of the driver 30 to climb the incline planes 25 of the wedge shaped drive head as a desirable torque limit is reached. The intersecting inclined planes 25 form an angle which can range between 15° and 60° but preferably form a 45° angle. The magnitude of the included angle of the drive head 24 geometry and the linear force applied to the drive handle 32 by the surgeon dictates the torque at which the driver 30 disengages from the head 24. A smaller included angle allows higher torques to be applied while a larger included angle will allow for lower torques to be applied prior to driver disengagement. Due to this ability, the design of the head can be set so that the driver 30 disengages prior to reaching torque levels that would induce mechanical failure in the head, neck, or shank of the screw 12.

Another unique feature of the fixation screw 12 is the tapered undercut 22 located between the drive head 24 and the threaded portion 16 of the screw (FIGS. 1 and 2). This tapered undercut feature accomplishes two ends. First, it acts to provide a gradual change in cross sectional geometry thus increasing the strength of the component under load and second it provides a tight engagement of the screw in the bone bore. In comparison to standard screw designs where the underside of the drive geometry sharply changes, the strength of the tapered undercut is far superior both under torque loading inherent in insertion and tensile loading post operatively.

Figure 6:
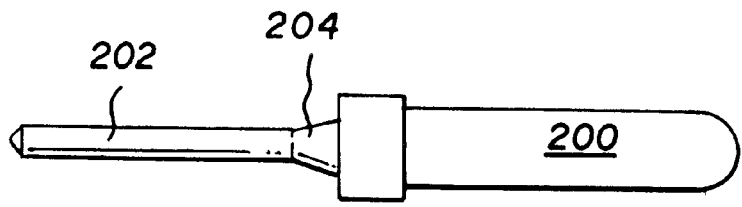
FIG. 6 shows a drill used to make the initial bore in a patient's bone.
Figure 7:
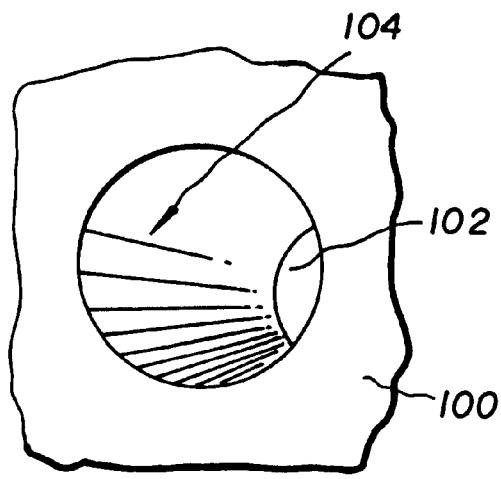
FIG. 7 is an enlarged perspective view of a mating taper cut in the bone wall.

The tapered undercut 22 also acts as a means of securing the screw 12 within the bone wall 100 after the drive head 24 has been cut flush with the bone surface. The taper allows for two means of securing fixation across the fracture or osteotomy. First, the taper feature allows for compression across the fracture site as would a conventional screw design. However, the taper also acts as a "taper lock" similar to those found in femoral head/femoral lock neck mating geometry's in Total Hip Replacement implants ensuring that even under cyclic loading conditions the screw will not "back out" of the threaded bone thus releasing the tension across the fracture or osteotomy (FIGS. 5 and 6).

Both the wedge shaped drive head 24 and the tapered undercut 22 serve to increase the strength of the screw 12 under torsion loading. Torsion loading induces tangential or planar shear stresses in planes normal to the longitudinal axis of the torque induced. The magnitude of these stresses is proportional to the cross section area of the material thus loaded. The shear stresses for the wedge shaped drive head 24 are related to torque as if set forth in the following equation $$T_{max} = t_{max} J/r;$$

Where:

$T_{max}$ is the maximum external twisting moment (torque induced by 'driver');

$t_{max}$ is the maximum unit shear stress of the material;

J is the polar moment of inertia for the cross section;

r is the radius of the cross section.

Or in more specific terms for circular cross sections:

$$T_{max} = (\pi/2) h^3 t_{max};$$

or . . .
Equation I $$T_{max} = 1.57 r^3 t_{max}$$

With respect to a modified Phillips Screw driver head with two orthogonal slots the resistance to torque may be approximated as:

$$T_{max}=(txy)_v+(txy)_m$$

$$(txy)_v = \frac{VO}{It}$$

WHERE: Q is the first moment; I is the second moment and t is the axis length (.7r): and $$(txy)_M = \frac{Tr}{J_o}$$

WHERE: T is the twisting course m and $J_o$ is the polar moment. Substituting these components one arrives at $$T_{max} = \frac{VO}{I(.7r)} + \frac{Tr}{J_o}$$

or . . .
Equation II $$T_{max}=0.079 t_{max} r^3$$

Figure 9:
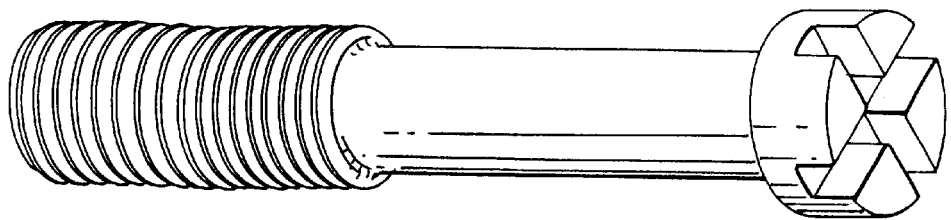
FIG. 9 is a perspective view of a screw with a prior art Phillips head.
Figure 10:
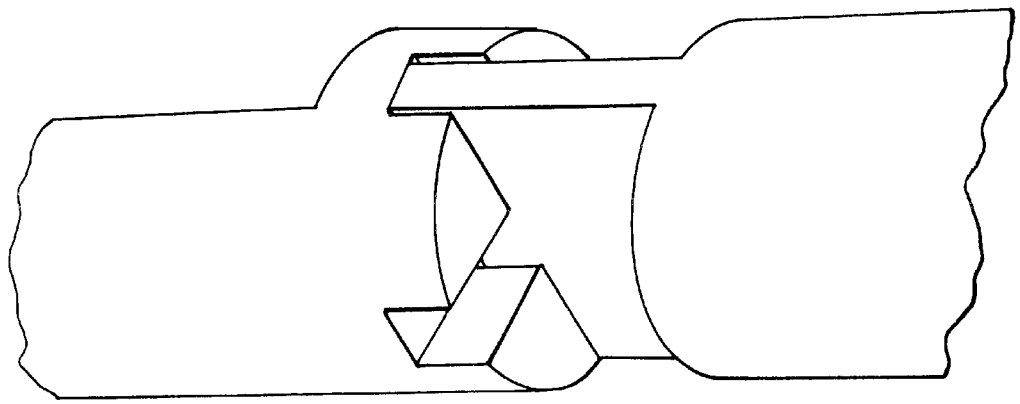
FIG. 10 is an enlarged view of a driver inserted in the Phillips head of the screw of FIG. 9.

Comparing the value of Equation II against Equation I, it can be readily be seen that the wedge shaped drive head 24 provides for a 20 fold increase in torsional loading strength with respect to the modified Phillips configuration shown in FIGS. 9 and 10. Such an increase in torsional loading strength is of great importance in allograft bone screws. It should be noted that no attempt has been made to include the effect of the stress riser in the Phillips type design. This factor is both geometry, material, and load rate dependent and can only serve to further reduce the strength of the Phillips style head with respect to the wedge shaped drive head. The wedge shaped drive head 24 and tapered undercut 22 of the screw 12 can also be formed of other biomaterial including, but not limited to, bioceramics, biocompatible/bioresorbable polymeric materials, biocompatible carbon fiber reinforced polymer and the multitude of orthopaedic inert implant metals including stainless steel, cobalt-chromium-molybdenum alloys, titanium and titanium alloys, tantalum and niobium and their alloys, HEDROCEL, a porous tantalum-carbon composite which has a modulus of elasticity that approximates that of human bone as well as other materials used in surgical applications.

The use of the implant driver 30 is shown with reference to FIGS. 4 and 5. The cylindrical shaft body 32 of the driver is formed with a cylindrical head 34 having a lesser diameter than shaft body 32 forming shoulder 33. The head 34 defines an angular "V" shaped notch or recess 36 at its distal end preferably of 45° or any other suitable angle which engages and seats the wedge shaped head 24 of screw 12 therein and applies a suitable amount of torque to the screw. A sleeve 38 having an inner diameter greater than the outer diameter of the head 34 but less than outer diameter of shaft 32 is seated on a shoulder 33 and holds screw head 24 within notch 36.

The inventive bone fixation screw was tested in a machine 300 as seen in FIG. 12. The machine 300 comprised a drilled and tapped block 302 and a counterbore block- unthreaded 304 into which screw 12 is mounted. The wedge shaped head 424 is shown extending from block 304. Blocks 302 and 304 were connected to a tensile test machine (not shown). Bone screws with a standard thread (UNC) and fabricated with the wedge head of the invention were tested to confirm the resistance to a torque load. A hole to match the screw thread (3.5 mm diameter, UNC thread) was drilled and tapped into block 302. The screw 12 is threaded through the unthreaded counter bore block 304 and tightened down.

Three different surgeons were separately observed to tighten the screw until each felt the screw to have the "right feel" of tightening. Each surgeon used a torque wrench to accomplish the tightening. The highest value of torque applied by any of the surgeons was 0.10 Newton-meters. This torque was then used to drive 52 screws into the threaded block 302. There were no instances when the wedge shaped head sheared off or mechanically failed with the 0.10 Newton-meters torque.

Two separate tests were undertaken. In the first test, the pull-out force was established. The screw was tightened in the test fixture 300 to the 0.10 Nm torque level. Tensile force was applied to the screw at a constant rate. The pull-out force averaged 557 Newtons (range 441–685). All samples broke at a point just at the beginning of the thread pattern. No failures occurred at or near the screw head.

In the second test the screws were separately tested to failure under a torque load. The screws were pre-tightened to the 0.10 Nm value and then torque continued to be applied until failure occurred. Torque failure averaged 0.24 Nm (range 0.214–0.276).

In operation of the assembly, a bore 102 is drilled in the patients bone 100 with the top section 104 or countersink of the bore 102 having a tapered geometry which widens from the diameter of the bore at the same angle as tapered portion 22. The bore can be cut in a single stage or two stage operation in which either the bore or the countersink is initially cut into the bone followed by the second cut. In the single stage cut, a drill 200 is provided with a drill bit 202 with a widened tapered portion 204 which enables drilling a bore with a tapered end section geometry 104 which is of the same size and configuration as the undercut 22 of screw 12. It will be appreciated that if the drive head 24 is to be totally contained within the fractured bone, that a first drill bore having a diameter greater than the widest diameter of screw 12 is cut in the bone followed by the previous noted drilling step. A bone screw comprising a shank with a uniform diameter threaded portion, an unthreaded portion with a outwardly tapered end and a driving head 24 of substantially wedge shaped configuration is seated in the wedge shaped notch seat 36 in the driver member head 34. The driver member is preferably constructed of steel and comprises a cylindrical shaft body 32, a cylindrical driver head 34 secured or integrally formed with the shaft body forming a shoulder 33 with the shaft body. A sleeve collar 38 is mounted around the driver head 34 engaging and seated on the shoulder 33. The screw 12 is driven into the previously cut bore 102 until the tapered portion 104 of the bore creates a mating surface for the tapered undercut 22 of the bone screw. The head 24 can be left extended from the bone surface, cut off or where the whole screw is countersunk, filled in with a flowable bone powder paste.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. A bone screw comprising a shank with a threaded portion and an unthreaded portion which tapers outwardly adjacent an integrally formed drive head to form a tapered undercut for the drive head, said tapered undercut being funnel shaped and tapered at an angle ranging from 10° to 45° from the center axis of the shank and has its greatest diameter adjacent said drive head, said drive head being substantially wedge shaped.

2. A bone screw as claimed in claim 1 wherein the screw is constructed of a biomaterial.

3. A bone screw constructed of allograft bone comprising a shank with a threaded portion and an unthreaded portion which tapers outwardly adjacent an integrally formed drive head to form a tapered undercut for the drive head, said tapered undercut being funnel shaped and tapered at an angle ranging from 10° to 45° from the center axis of the shank and has its greatest diameter adjacent said drive head, said drive head being provided with at least two flat surfaces adapted to engage a driving tool and receive torque from said driving tool.

4. A bone screw as claimed in claim 2 wherein said biomaterial is bioceramics.

5. A bone screw as claimed in claim 2 wherein said biomaterial is a biocompatible/bioresorbable polymeric material.

6. A bone screw as claimed in claim 1 wherein said screw is constructed of an inert metal.

7. A bone screw as claimed in claim 6 wherein said inert metal is stainless steel.

8. A bone screw as claimed in claim 6 wherein said inert metal is titanium.

9. A bone screw as claimed in claim 6 wherein said inert metal is a titanium alloy.

10. A bone screw as claimed in claim 6 wherein said inert metal is tantalum.

11. A bone screw as claimed in claim 6 wherein said inert metal is a tantalum alloy.

12. A bone screw as claimed in claim 6 wherein said inert metal is niobium.

13. A bone screw as claimed in claim 6 wherein said inert metal is a niobium alloy.

14. A bone screw as claimed in claim 6 wherein said inert metal is cobalt-chromium -molybdenum alloy.

15. A bone screw as claimed in claim 6 wherein said inert metal is HEDROCEL, a porous tantalum-carbon composite.

16. A bone screw as claimed in claim 6 wherein said tapered undercut when extended to intersect a longitudinal center axis of said shank forms an angle of about 20°.

17. A bone screw as claimed in claim 6 wherein said tapered undercut when extended to intersect a longitudinal center axis of said shank forms an angle ranging from about 10° to about 20°.

18. A bone screw as claimed in claim 6 wherein said tapered undercut when extended to intersect a longitudinal center axis of said shank forms an angle ranging from about 20° to about 30°.

19. A bone screw as claimed in claim 3 wherein said bone screw has a torque shear of at least 0.10 Newton-meters.

20. A bone screw as claimed in claim 3 wherein said bone screw has a torque shear of at least 0.20 Newton-meters.

21. A bone screw as claimed in claim 3 wherein said bone screw has a torque shear ranging from about 0.214 Newton-meters to about 0.276 Newton-meters.

22. A bone screw as claimed in claim 3 wherein said bone screw has a pullout force ranging from 440–685 Newtons.

23. A bone screw constructed of allograft bone comprising: a shank with a portion provided with a thread of a given pitch running along a portion of its length and terminating in a conical end; an unthreaded portion of said shank is formed with an outwardly flaring section having a diameter which is greater than the diameter of said threaded portion, said outwardly flaring section being located adjacent to and integrally formed with a screw head having a wedge shape configuration with angular inclined planes.

24. A bone screw as claimed in claim 23 wherein said screw is threaded about ½ the length of the shank.

25. A bone screw as claimed in claim 23 wherein the wedge shaped drive head has a shear stress in relation to torque calculated by the formula $T_{max}=1.57\ r^3 t_{max}$.

26. A bone screw as claimed in claim 23 wherein said bone screw is constructed of cortical allograft bone.

27. A bone screw as claimed in claim 23 wherein said bone screw is constructed of cancellous allograft bone.

28. A bone screw as claimed in claim 23 wherein said angular inclined planes when intersected form an angle ranging between about 15° and about 60°.

29. A bone screw constructed of allograft bone comprising a shank with a substantially uniform diameter threaded portion having a distal pointed end and an unthreaded portion adjacent said threaded portion, said unthreaded portion defining an outwardly tapered end with a male wedge shaped driving head defining inclined planes, said bone screw having a shear stress in relation to torque calculated by the formula $T_{max}=1.57\ r^3 t_{max}$ with said unthreaded outwardly tapered end forming a tapered undercut for said male wedge shaped driving head at an angle less than the angle formed by the inclined planes of said driving head.

30. A bone screw as claimed in claim 29 wherein said wedge shaped driving head forms an angle ranging from about 10° to about 60°.

31. A bone screw as claimed in claim 29 wherein said tapered undercut forms an angle with the center axis of the shank ranging from about 10° to about 45°.

32. A bone screw as claimed in claim 1 wherein said wedge shaped driving head forms an angle on its distal end which allows disengagement from a driver assembly when a predetermined torque is applied.

33. A bone screw comprising a shank with a threaded portion and an unthreaded portion which tapers outwardly adjacent an integrally formed drive head to form a tapered undercut for the drive head, said screw being threaded about ½ the length of its shank and ranging in length from 1 to 1.25 inches, said drive head being substantially wedge shaped.

34. A bone screw constructed of allograft bone comprising a shank with a threaded portion and an unthreaded portion which tapers outwardly adjacent an integrally formed drive head to form a tapered undercut for the drive head, said drive head being substantially wedge shaped, said wedge shaped drive head having a shear stress in relation to torque determined by the formula $T_{max}=1.57\ r^3 t_{max}$.

35. A bone screw as claimed in claim 34 wherein said allograft bone is cortical bone.

36. A bone screw constructed of allograft bone comprising a shank with a threaded portion and an unthreaded portion which tapers outwardly adjacent an integrally formed drive head to form a tapered undercut for the drive head, said tapered undercut having a cross sectional area taken transverse a central axis of said screw across its distal end which is greater than a cross sectional area taken transverse to a central axis of said screw across the unthreaded portion of the shank, said tapered undercut when extended to intersect a longitudinal center axis of said shank forming an angle ranging from about 20° to about 30°, said drive head being provided with at least two flat surfaces adapted to receive torque from a driver.

37. A bone screw as claimed in claim 36 wherein said tapered undercut is funnel shaped and ends at one end of said drive head.

38. A bone screw as claimed in claim 36 wherein said screw is threaded about ½ the total length of the screw.

* * * * *